Figure 1:
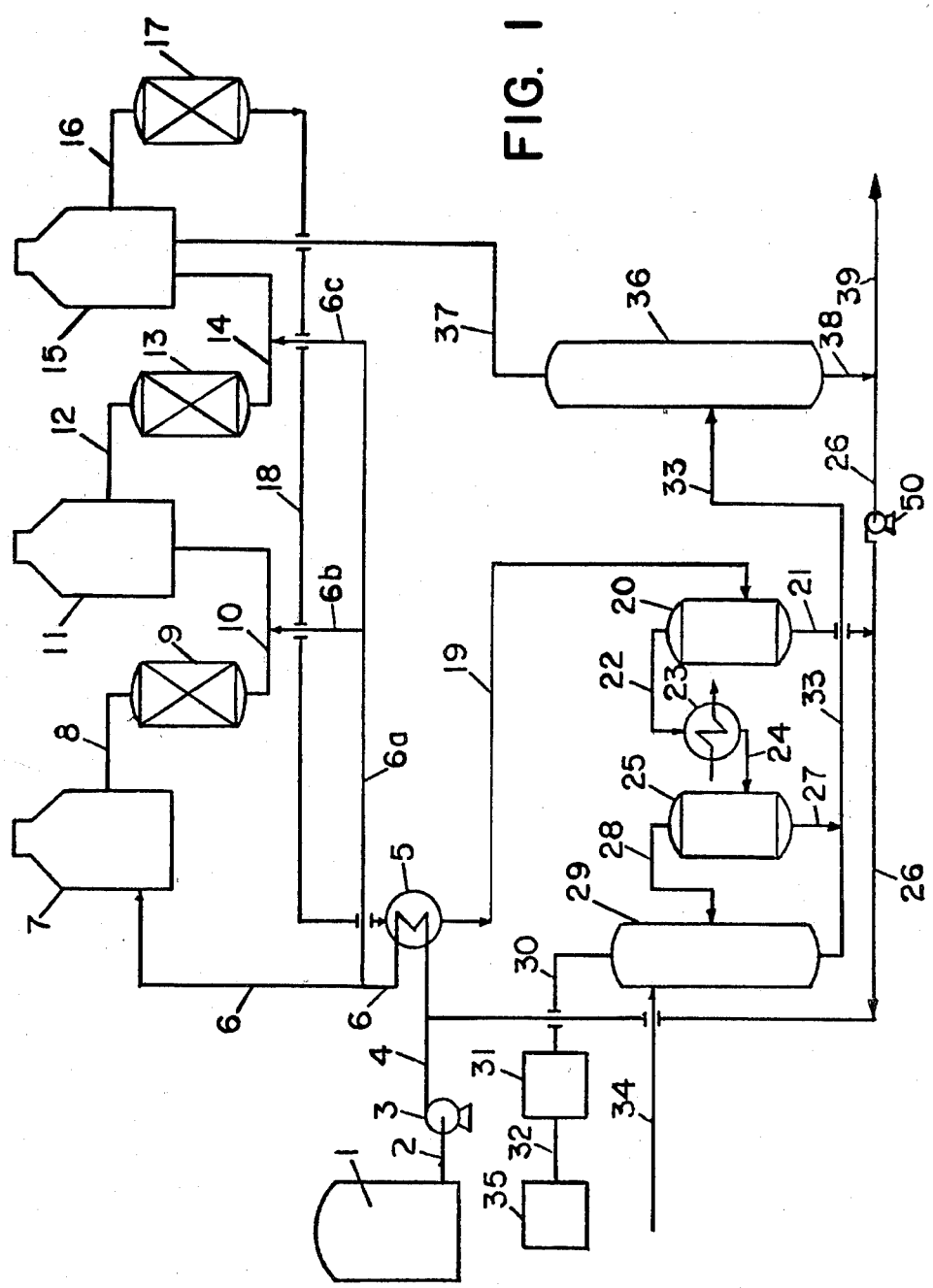

United States Patent [19]

Barrocas et al.

[11] 4,396,789

[45] Aug. 2, 1983

[54] PROCESS FOR DEHYDRATION OF A LOW MOLECULAR WEIGHT ALCOHOL

[75] Inventors: Hélcio V. Barrocas; Fernando Baratelli Júnior, both of Rio de Janeiro, Brazil

[73] Assignee: Petroleo Brasileiro S.A., Rio de Janeiro, Brazil

[21] Appl. No.: 357,180

[22] Filed: Mar. 11, 1982

[30] Foreign Application Priority Data

Mar. 13, 1981 [BR] Brazil ................................. 8101487

[51] Int. Cl.³ ............................................. C07C 1/24
[52] U.S. Cl. ..................................... 585/639; 585/640
[58] Field of Search ......................... 585/639, 640, 698

[56] References Cited

U.S. PATENT DOCUMENTS 3,121,758  2/1964  Rylander et al. ................... 585/639
4,232,179 11/1980  Barrocas et al. .................... 585/640
4,234,752 11/1980  Wu et al. ............................ 585/640

FOREIGN PATENT DOCUMENTS 557378  4/1947  United Kingdom ................ 585/640

Primary Examiner—Delbert E. Gantz
Assistant Examiner—A. Pal
Attorney, Agent, or Firm—Bert J. Lewen

[57] ABSTRACT

This invention relates to a process for the dehydration of ethanol to form ethene in fixed adiabatic reactors containing a dehydration catalyst. The process includes the recycling of unreacted ethanol to the process, feeding the charge to the initial reactor at a pressure of 20 to 40 atmospheres, withdrawing the ethene from the final reactor at a pressure of no less than 18 atmospheres, and passing at least a portion of said reaction effluent to cryogenic purification with further compression.

3 Claims, 2 Drawing Figures

PROCESS FOR DEHYDRATION OF A LOW MOLECULAR WEIGHT ALCOHOL

This invention relates to a process for the dehydration of a low molecular weight alcohol, which consists mainly of an integrated process to dehydrate ethanol in the presence of a catalyst in adiabatic reactors at high pressures, with the application of heat in intermediate stages, so that the ethene withdrawn from the reactor is at a pressure sufficiently high so as not to require compressing prior to purification thereof by cryogenic distillation.

In catalytic dehydration processes of ethanol, the ethene withdrawn from the final stage is usually at a pressure which is not very high. Accordingly, to perform cryogenic distillation, to obtain high purity ethene useful for polymerization, compression is required.

The loss of pressure that occurs during conventional processes results from the several heat exchange and intermediate separation operations that take place before the products go to the final purifying stage. In such prior art processes the compressing and cooling prior to the final purifying stage is disadvantagous because much power is consumed, the cost of compression is high and additional ancillary operations are necessary. This substantial amount of operation cost should obviously be eliminated or minimized.

The present invention now provides a process which integrates 'heat exchange' and 'operational pressure' in such a way that the ethene from the final stage only needs to undergo a cooling stage before going directly to purification by cryogenic distillation. Furthermore, in the course of the process, there is heat exchange between the several streams of the process and the recycling of unreacted substances, of part of the water formed during the process, and of the water added for the final washing of vapors.

The practice of catalytically dehydrating ethanol is based on work done by Sabatier, Ipatief and others at the beginning of the century. They were initially concerned about the specific substances useful as catalysts. Thus temperature conditions and dehydration yields were developed for various metals and oxides of metals so that the gaseous reactants would be constantly in contact with the solid catalyst. On the strength of such principles, the experimental laboratory processes were scaled up to industrial size without any change in the theoretical principles used in pioneering experimental work. Thus basic operational procedure called for maintaining flow rates of alcohol vapor, at near atmospheric pressure, across the fixed bed of oxide (catalysts) so as to achieve the desired conversion. Because of the highly endothermic nature of the reaction the bed of the catalyst was held at a reasonably high constant temperature by direct heating thereof or by the use of molten salts.

Generally both temperature and flow were controlled to prevent the formation of undesirable by-products (e.g. ether) which lower the yield. If temperature was too high and/or flow too low, undesirable by-products were formed. If flow was increased, the conversion of ethanol into ethene would drop.

Naturally the water and unreacted alcohol could be added gradually to the fresh charge and be reprocessed afterwards. But such procedure was also restricted by the required raw material composition. Low concentration of alcohol would prevent any reaction of the feed under the standard operating conditions.

To avoid such difficulties, U.S. Pat. No. 4,232,179 teaches a process which is much more advanced than the ones conventionally used. In that patent a method of making ethene from ethanol is described, whereby there is no need to constantly and uniformly heat the bed of the catalyst. Instead, the reactor containing the catalyst is adiabatic; products arrive at the bed at a temperature high enough to achieve contact between the alcohol and the catalyst in the reactor at a temperature at which the reaction can proceed normally.

The question of recycling the unreacted alcohol and water from the last reactor does not arise, because in this process there is heat exchange between the feed and product streams and any unreacted products are recycled at inner stages of the process.

Those skilled in the art will recognize that in the process of the above described invention, the temperature of the bed depends solely on the heat supplied externally to the raw material and to a heat-bearing stream of liquid. If products flow to the reactor is discontinued, there will be a break in the heat fed to the system and temperature of the latter will drop naturally. There is no need to turn off the fuel that heats the bed nor the apparatus that circulates the molten salts. Likewise, flow of products and recycling thereof and any heat exchanges can be made to start up again at any time, without the need to slowly heat the reactor. Initially, recycling control is all that is required to build up to the desired reaction rate.

This one point alone is a major technical advance. Less time and effort are needed to control the process.

Process conditions under the aforesaid U.S. Pat. No. 4,232,179 were already such as to allow for operating pressures well above atmospheric pressure. However, owing to kinetic limitations, at the time that process was developed it was considered difficult to achieve pressures above 20 atm.

Because very high pressures could not be used it was necessary to use compressor equipment to keep the final ethene in a state suitable for purification by cryogenic means. If high pressures could be used, the ethene need only be finally dried and cooled to achieve a state suitable for purification by cryogenic distillation. This in turn means that a safer control of temperatures can take place over the several stages of purification and recycling.

An outstanding point of this invention as compared with that in U.S. Pat. No. 4,232,179, the disclosure of which is incorporated by reference herein, is that from the time that the ethanol is first taken out of stock to when it is combined with the recycle stream, high pressure is made to act upon the charge which is being processed, throughout all intermediate dehydration and purification stages. Additionally, the final product can be fed to the cryogenic distillation stage without need for any further compression.

It is clear that in the process of this invention the several stages work together so that the exchange of heat takes place with the least possible loss. The pressure drop through the whole circuit is such that, at the point where product is finally withdrawn, the pressure is at least 18 atmospheres.

As stated above, the dehydration can be carried out with steam as the heat-bearing fluid, at pressures that are quite high. Individual conversion rates are higher than 96% by weight and, at recycling stages, where unconverted alcohol is being recovered, the yield is near theoretical.

Figure 2:
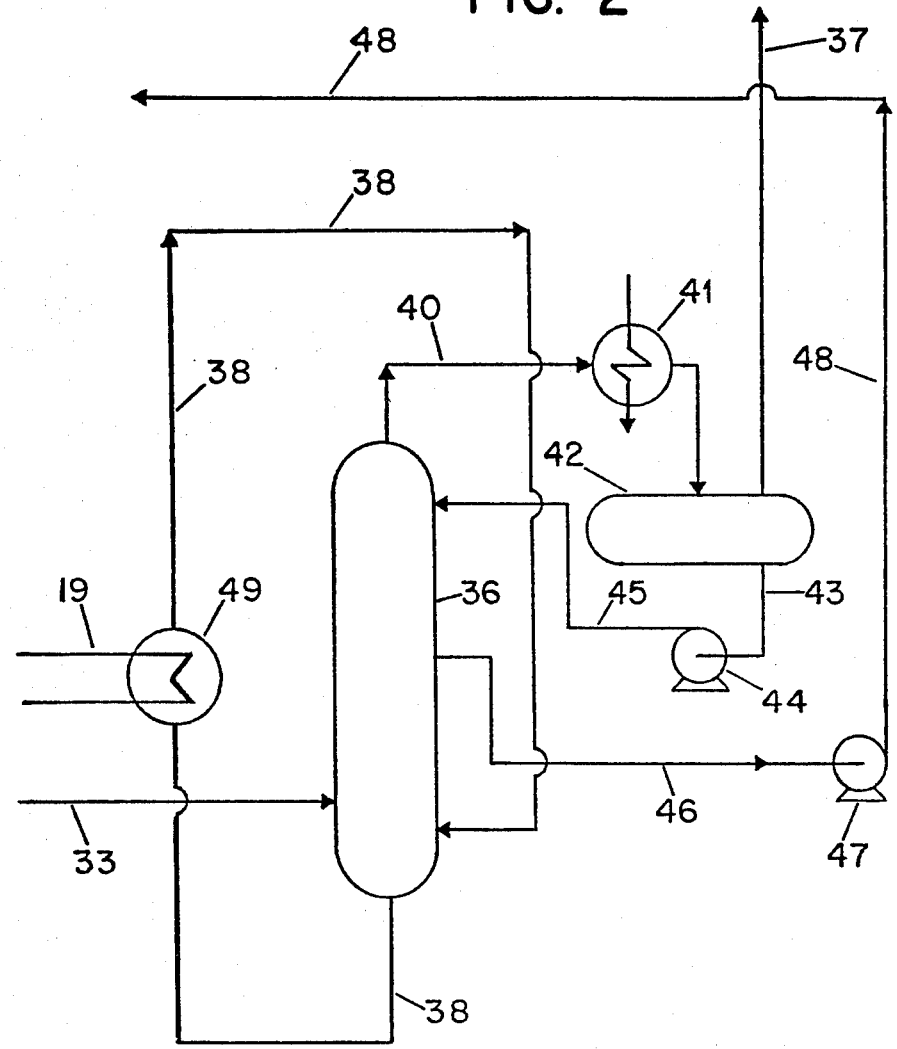

The foregoing and other objects, characteristics and advantages of the present invention will be more clearly understood from the following detailed description of preferred embodiments thereof when read in conjunction with the accompanying drawings, in which:

FIG. 1 is a schematic illustration of the manner of practicing the process of the present invention; and FIG. 2 is a schematic illustration of certain alternatives to the steps shown in FIG. 1.

More particularly, FIG. 1 is a simplified diagram which shows the major operations in the process. It should be understood that this scheme is provided merely as an example of the invention and is not intended to be limiting. It should also be mentioned that certain stages have been condensed for simplicity and conventional equipment not essential to an understanding of the process is not shown.

From storage tank 1 the alcohol is carried by line 2 to pump 3. A conduit 26 feeds recycled water along with the remains of alcohol into line 4, which come from intermediate purification stages of the products. Pump 3 compresses the material from line 2 to between 20 and 40 atm. The effluent issues from line 4 and passes to heat exchanger 5 where heat is exchanged with the product that leaves the last reactor 17 of the series of reactors via line 18. The vaporized, heated, and compressed matter that leaves the heat exchanger 5 is conducted off via line 6. A portion of the product in line 6 goes to furnace 7 from where it issues along line 8 on its way to adiabatic reactor 9. The reactor 9 is filled with a catalyst, e.g. one of those disclosed in U.S. Pat. No. 4,232,179, that is suitable for the dehydration of alcohol. Reaction products come out via line 10 and enter furnace 11 where they are heated to the same temperature as the charge that runs along line 8.

The heated mixture comes out of furnace 11 by line 12 and passes through reactor 13, also filled with a catalyst of the aforesaid types.

The reaction products from the reactor 13 issue by line 14 and pass to furnace 15 where they are heated to a temperature equal to that of the charge fed into reactors 9 and 13. The product that comes out of furnace 15 flows via line 16 at a temperature which is the same as that of the product fed into the previous reactors. This product goes to reactor 17 where practically all of the alochol which had failed to react previously is dehydrated.

Part of the charge vaporized in heat exchanger 5 runs along line 6a and splits off at lines 6b and 6c into lines 10 and 14, respectively, to join the charges which are heated in furnaces 11 and 15.

The product which issues from reactor 17, which is the last of the series of reactors, is carried along line 18 to the stages of the process where liquids and gases are separated and where final purification takes place. Enroute to these stages the product flows through heat exchanger 5 where it heats and vaporizes the fresh incoming feed. From heat exchanger 5, the product goes via line 19 to separator 20 which separates liquids from gases. Gaseous products are removed via line 22, cooled in a water-cooled heat exchanger 23 and carried via line 24 to separator 25. The liquid products from separator 20 run via line 27 to line 26, the return line for product recycle.

From separator 25 the gaseous products flow by line 28 to gas washer 29 where they contact a stream of wash water which is fed via line 34.

Though the streams of gas given off by separator 20 along line 22 and by separator 25 along line 28 are rich in ethene, they still contain a small quantity of residual alcohol, entrained moisture and perhaps undesirable by-products (such as ether) which must be separated. The material in line 28 is subjected to final washing in gas washer 29. The exit gas in line 30 will be made up almost entirely of ethene (with a minute quantity of moisture). It flows to the drier and cooler 31 from where it leaves by line 32 and goes to the cryogenic distillation stage 35.

This invention is so planned that from initial compression at 3 to cryogenic distillation at 35, pressure drop is such that when ethene reaches the final purification stage its pressure is at least 18 atm. The only additional pressure required is that needed for the intermediate pumping of streams of liquids.

The stream of liquid that comes out of washer 29 via line 33 contains water and a certain amount of residual alcohol. At a certain point along the way this stream of liquid in line 33 joins the stream of liquid in line 27 emanating from separator 25. The combined stream goes to separation column 36. From this separation column 36, shown in simplified form, watery residue issues along line 38. The residue is divided, a part being carried via line 39 to the stream of treated effluents and the other part being recycled via line 26 to the feed stream line 4. Thus the stream of waste given off by line 39 will be practically free from any kind of organic matter connected with the process and will not be regarded as polluting waste.

Since the feed stream line 4 is at a high pressure any incoming stream of water and recycled matter must also be under high pressure. This pressure is provided by pump 50 in line 26.

The simplified separation represented in FIG. 1 shows that certain of the effluents from separators 20 and 25 and from gas washer 29 are passed to separation column 36, a stage where the unconverted alcohol is recovered and where part of the watery output which contains residual alcohol is recycled. Heat exchange between the several streams may result in additional savings.

It should be stressed and those skilled in the art will realize that the arrangement of a separator of this kind involves operations which may be more intricate than those shown in FIG. 1. FIG. 2 exemplifies alternative paths for the flow of the several streams of products.

In FIG. 2 the stream of liquid which is separated at several stages of the operation passes via line 33 and to a certain point of column 36, where it is separated into a gas stream and a liquid residue. The gaseous product which comes out at the top through line 40 undergoes heat exchange with cold water in heat exchanger 41 and carries on to a separation drum 42. The liquid equilibrium stream from said drum 42 is withdrawn from the bottom thereof along line 43 and pumped by pump 44 back to column 36 via line 45. The gaseous equilibrium product from separation drum 42 flows along line 37 to feed furnace 15 which is upstream from adiabatic reactor 17, as shown in FIG. 1.

The liquid product that comes out at the bottom of separator 36 via line 38 undergoes heat exchange in heat exchanger 49 with heated products in line 19, and is recycled back to the appropriate location in column 36.

The stream acts as a heat-bearing fluid. From column 36 a stream of liquid rich in water is withdrawn via line 46, from which it is pumped by pump 47 to line 26 (not shown in FIG. 2) via line 48.

The configuration in FIG. 2 serves to show how portions of intermediate recycled streams can be introduced to enrich other streams with desirable products and thus significantly enhance overall efficiency, without going to external processing.

Generally, the process of catalytic dehydration of ethanol in a plurality of fixed bed adiabatic reactors wherein the reaction products are finally purified in a cryogenic distillation stage, is characterized by the fact that the ethanol is introduced into the first reactor (and if desired also into each other reactor) at a temperature of from 400° to 520° C. and at a pressure of from 20 to 40 atmospheres, that the reaction product is withdrawn from the last reactor at a pressure of at least 18 atmospheres, and that at least a portion of the said reaction product, after cooling, is passed to the cryogenic distillation stage without further compression. The plurality of reactors may be connected in series or in parallel. Another characteristic is that the effluent from the last reactor is used to vaporize the feed to the first reactor, and yet another that the unreacted ethanol separated from the reactor effluent is recycled to the process to ensure substantially complete conversion to ethene.

As an example of how the process covered by this invention takes place, data taken from a typical run are given below:

1. Pressure of alcohol and water vapors in line 4, downstream of pump 3 and of current fed in by line 26: 4 atm.
2. Temperature at inlet to reactors 9, 13 and 17: 470° C.
3. Temperature at outlet of reactors 9, 13 and 17: 360° C.
4. Pressure at inlet to reactor 7: 40 atm.
5. Pressure at inlet to reactor 13: 38 atm.
6. Pressure at inlet to reactor 17: 36 atm.
7. Overall rate of conversion of ethanol into ethene from a battery of three in series adiabatic reactors: 92.23% by weight.
8. Pressure of ethene produced, before final cooling: 34 atm.
9. Temperature of ethene before final cooling: 30° C.

Ethene obtained in accordance with this example is of high purity and suitable for polymerization.

What is claimed is:

1. A process for the production of high purity ethene from ethyl alcohol in a plurality of adiabatic reactors containing a fixed bed catalyst which comprises:
   (i) introducing ethyl alcohol and steam at a temperature of from 400° to 520° C. and a pressure of from 20 to 40 atm. into the first of the adiabatic reactors, thereby dehydrating a portion of said ethyl alcohol;
   (ii) withdrawing at a pressure of not less than 18 atm. from the last of the adiabatic reactors a hot reaction product containing ethene, water and unreacted alcohol;
   (iii) separating from said reaction product ethene and water formed during the reaction;
   (iv) washing the ethene obtained from step (iii) to separate trace amounts of unreacted ethyl alcohol;
   (v) heating at least a portion of the wash water from step (iv) and the water formed in the reaction by heat exchanging such water with the hot reaction products from the last adiabatic reactor to form steam;
   (vi) directly contacting the steam formed in step (v) and ethyl alcohol to form the feed to the first adiabatic reactor;
   (vii) cooling the washed ethene from step (iv) above and passing said cooled ethene to a high pressure cryogenic distillation stage to obtain a high purity ethene, said high pressure required for the cryogenic distillation stage being achieved by the compression of the feed to the dehydration process.

2. The process of claim 1 wherein the plurality of reactors are connected in series.

3. The process of claim 1 wherein the plurality of reactors are connected in parallel.

* * * * *

UNITED STATES PATENT AND TRADEMARK OFFICE
CERTIFICATE OF CORRECTION

PATENT NO. : 4,396,789
DATED : Aug. 2, 1983
INVENTOR(S) : Helcio V. Barrocas and Fernando Baratelli Junior It is certified that error appears in the above-identified patent and that said Letters Patent are hereby corrected as shown below:

Column 5, line 36: delete "4 atm." and substitute --40 atm.--.

Column 5, line 41: delete "7" and substitute --9--.

Signed and Sealed this

Eleventh Day of October 1983

[SEAL]

Attest:

GERALD J. MOSSINGHOFF

Attesting Officer

Commissioner of Patents and Trademarks